United States Patent
Liao et al.

(10) Patent No.: US 10,849,861 B2
(45) Date of Patent: Dec. 1, 2020

(54) PHARMACEUTICAL COMPOUND FOR TREATING COLORECTAL CANCER

(71) Applicants: Everest Pharm. Industrial Co., LTD., Minxiong Township, Chiayi County (TW); Se-Chun Liao, Minxiong Township, Chiayi County (TW)

(72) Inventors: Se-Chun Liao, Minxiong Township, Chiayi County (TW); Su-Fen Chen, Minxiong Township, Chiayi County (TW)

(73) Assignees: EVEREST PHARM. INDUSTRIAL CO., LTD., Chiayi County (TW); Se-Chun Liao, Chiayi (TW)

( * ) Notice: Subject to any disclaimer, the term of this patent is extended or adjusted under 35 U.S.C. 154(b) by 0 days.

(21) Appl. No.: 16/529,366

(22) Filed: Aug. 1, 2019

(65) Prior Publication Data

US 2020/0038340 A1   Feb. 6, 2020

(30) Foreign Application Priority Data

Aug. 3, 2018 (TW) ............................. 107127143 A

(51) Int. Cl.
  *A61K 31/05* (2006.01)
  *A61P 35/00* (2006.01)
(52) U.S. Cl.
  CPC .............. *A61K 31/05* (2013.01); *A61P 35/00* (2018.01)

(58) Field of Classification Search
  CPC ................................ A61K 31/05; A61P 35/00
  USPC .......................................................... 514/733
  See application file for complete search history.

(56) References Cited

U.S. PATENT DOCUMENTS 9,980,979 B2 * 5/2018 Wu .......................... A61P 19/08

OTHER PUBLICATIONS

Lin et al., International J Oncology, (2016), V49, p. 629-638.*
Ryu et al., Archives of Pharmacal Research, (2002), 25(5), p. 636-639.*
Sainz et al., Cancers, (2002), V.4, p. 442-474.*
Tessitore et al., Carcinogenesis, (2000), V21, p. 1619-1622.*
Wolter et al., J. Nutr., (2002), v25, p. 298-302.*
Office Action issued in corresponding TW Application No. 107127143 dated Mar. 27, 2019 and response, 8 pages.
Patent approval notice issued in corresponding TW Application No. 107127143 dated Jul. 12, 2019, 2 pages.

* cited by examiner

*Primary Examiner* — Yong L Chu
(74) *Attorney, Agent, or Firm* — Muncy, Geissler, Olds & Lowe, P.C.

(57) ABSTRACT

A pharmaceutical compound TG1 (2, 3, 5, 4'-tetrahydroxy-trans-stilbene) and a new use for treating colorectal cancer thereof are provided. The pharmaceutical composition of the present invention has the structure of formula shown as below. Each variable in formula I and treating method are detailed in the specification.

5 Claims, 10 Drawing Sheets

PHARMACEUTICAL COMPOUND FOR TREATING COLORECTAL CANCER

RELATED APPLICATIONS

This Non-provisional application claims priority under 35 U.S.C. § 119(a) on Patent Application No(s). 107127143 filed in Taiwan, Republic of China, Aug. 3, 2018, the entire contents of which are hereby incorporated by reference.

FIELD OF THE INVENTION

The present invention relates to a pharmaceutical compound TG1 (2, 3, 5, 4'-tetrahydroxy-trans-stilbene), which has a new use for treating colorectal cancer.

BACKGROUND OF INVENTION

In Taiwan, the incidence and mortality of colorectal cancer are increasing rapidly every year, which ranks the second and third place in the incidence and mortality of all cancers. Most of colorectal cancer originates from living habits and aging, and a few from genetic diseases.

Colorectal cancer treatment includes surgery, radiation therapy, chemotherapy, and targeted therapy, or a combination of these therapies. Colorectal cancer, which is confined to the intestinal wall, may be cured by surgery. In the U.S., the 5-year survival rate is about 65%. However, it depends mainly on the patients' health and cancer stage, and staging is related to whether it can be removed by surgery. Overall, colorectal cancer is the third common cancer, accounting for about 10%. Colorectal cancer is more common in developed countries, accounting for 65% of the total number of cases in the world. It is rare in women than in men.

Surgery is the most important method for treating colorectal cancer. Except for the fourth stage, basically surgical resection will be recommended for $1^{st}$~$3^{rd}$ stage. However, after the examination and evaluation, if the tumor position is close to the anus, it may be anal. The anus cannot be retained, the artificial anus is needed to install, it is difficult for most people to accept, therefore, it is recommended to use chemotherapy or chemotherapy together with radiation therapy before surgery, when the tumor is reduced and then surgery, the anus may be retained, and it can reduce the chance of local recurrence, but the side effects of radiotherapy and chemotherapy are large, and it is not accepted by the general public. Therefore, a specific drug for reducing colorectal cancer tumor is needed to replace radiation therapy and chemotherapy, so as to satisfy the need for treatment.

In current preclinical studies, it is shown that the resveratrol has many biological activities and it can be used to prevent and/or treat cancer, cardiovascular disease and neurodegenerative diseases. Resveratrol is a natural polyphenolic compound in the peanut, grape, red wine and some berries. The resveratrol is well absorbed when taken orally. Although many previous literatures have revealed the biological activity of resveratrol, but there is no evidence to infer the resveratrol or its derivatives, which has a specific poisoning effect on specific cancers.

The previous literature (Saunier, Elise, et al. "Resveratrol reverses the Warburg effect by targeting the pyruvate dehydrogenase complex in colon cancer cells." Scientific reports 7.1 (2017): 6945) reveals the role of the resveratrol-induced apoptosis, there are different reactions in different human cancer cells. The literature further indicates that resveratrol has no any ability to inhibit cancer cells in human colorectal cancer (Caco2, SW480, HCT116). It can be known that the biological activity of resveratrol has been seen in the prior art, but there is no evidence to prove that resveratrol or its derivatives have specific poisoning ability against human colorectal cancer cells.

In summary, because colorectal cancer uses a medical composition with less side effects for poisoning the colorectal cancer cells before surgery, the tumor is reduced, and then surgery or the surgery is not required by the early detection, retaining the anus and reducing the chance of local recurrence, increasing the patient's willingness to seek medical treatment, early detection for early treatment, increasing the survival period of the patient is an urgent problem to be solved, therefore, the industry urgently needs to develop a pharmaceutical compound that specifically poisons colorectal cancer cells for treating colorectal cancer.

SUMMARY OF THE INVENTION

In view of this, the present invention provides a pharmaceutical compound TG1 (2, 3, 5, 4'-tetrahydroxy-trans-stilbene), which has a new use for treating colorectal cancer.

The present invention provides a pharmaceutical compound, as shown in Eq. I.

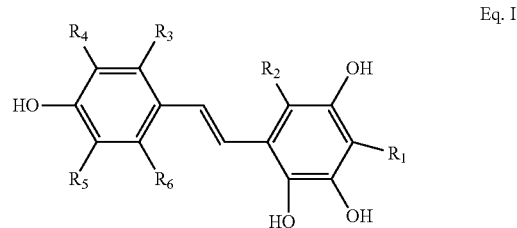

Eq. I wherein: R1, R2, R3, R4, R5 and R6 comprise —H, —NH2, —OH, —C=O, or a substituent which increases the water solubility of the pharmaceutical compound; or a pharmaceutically acceptable cis-trans isomer thereof.

The present invention provides the pharmaceutical compound, wherein the R1, R2, R3, R4, R5 and R6 are selected from the group consisting of —NH2, —OH, —C=O, or a substituent which increases the water solubility of the pharmaceutical compound, the substituent with polarization covalent bond can form an acting force with water, thus increasing the hydrophilic polarity.

The present invention provides the use for the preparation of a medicament for treating colorectal cancer, wherein the medicament comprises a pharmaceutical compound as shown in formula I, and a pharmaceutically acceptable supporting agent, adjuvant or vehicle.

The present invention provides the use for the preparation of a medicament for treating colorectal cancer, wherein the medicament comprises a TG1 (2, 3, 5, 4'-tetrahydroxy-trans-stilbene) pharmaceutical compound, a pharmaceutically acceptable supporting agent, adjuvant or vehicle.

The invention provides a medicament for the preparation of a medicament for treating colorectal cancer, wherein the medicament has no significant growth inhibiting effect on other types such as breast cancer, lung cancer and lymphoma.

The term "colorectal cancer" as used in the present invention refers to a cancer originating from the colon or the rectum (part of the large intestine), including the invasion or metastasis of cancer cells to other parts of the body.

The term "colorectal cancer" as used in the present invention, which comprises cancer cells with MSI+, CIN+, CIMP+, TGF-β, KRAS mutation or BRAF mutation, may be in the form of Tubular adenoma, Villous adenoma or Serrated adenoma.

The pharmaceutical compound provided by the present invention comprises the message pathway inhibiting the β-catenin and promoting apoptosis of cancer cells, mainly to increase the ratio of Bax/Bcl-2 in the cells, increase the activation of caspase-3, so as to split the DNA repairase PARP, thereby opening the cancer cell apoptosis effect.

In order to achieve the above and other objects, one or more specific embodiments of the present invention are described below. Other features or advantages of the present invention are described in detail in the embodiments and requests.

DETAILED DESCRIPTION OF THE INVENTION

Embodiment 1, a Method for Synthesizing TG1 (2, 3, 5, 4'-tetrahydroxy-trans-stilbene)

In a scope of the present invention, the present invention provides a pharmaceutical compound as shown in Eq. I.

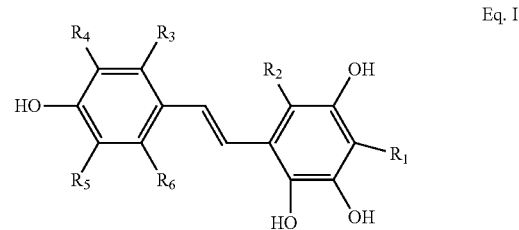

Eq. I wherein: R1, R2, R3, R4, R5 and R6 comprise —H, —NH2, —OH, —C=O, or a substituent which increases the water solubility of the pharmaceutical compound; or a pharmaceutically acceptable cis-trans isomer thereof.

Figure 1:
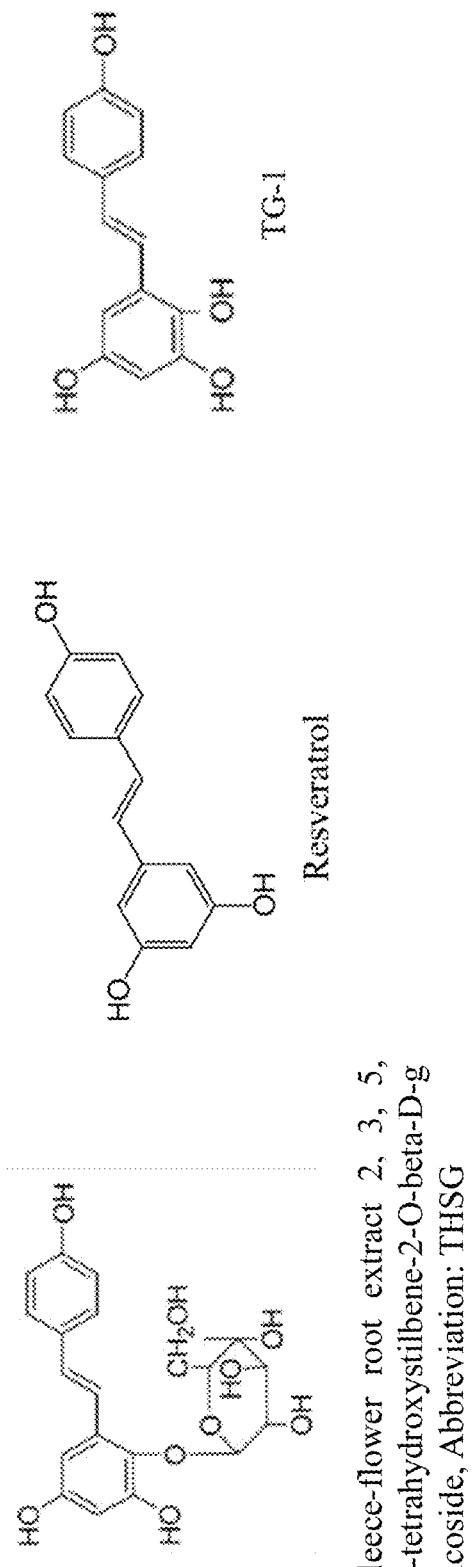
FIG. 1 shows the produce TG1 of active ingredient THSG (2, 3, 5, 4'-tetrahydroxystilbene-2-O-beta-D-glucoside) of the aqueous extract of fleece-flower root after modification of its functional group.

Referring to FIG. 1, the synthesis method of TG1 (2, 3, 4'-tetrahydroxy-trans-stilbene) is the active ingredient THSG (2, 3, 5, 4'-tetrahydroxystilbene-2-O-beta-D-glucoside) of the aqueous extract of fleece-flower root after modification of its functional group, the related synthesis method is shown in Step (1)-(3).

(1) THSG (2.06 g, 5.62 mmol) is dissolved in ethanol (50 ml) in a round bottom flask, hydrochloric acid (1.0 M, 75 ml) is added, refluxed and heated to 70° C. and reacted for 18 hours. (2) After cooled to room temperature, the ethanol is removed by a cyclone concentrator, and the aqueous solution is extracted with diethyl ether. After removing the ether, the residual water in diethyl ether is removed by anhydrous magnesium sulfate. After removing magnesium sulfate by filtration, the ether is drained by a cyclone concentrator. (3) The product is purified by normal phase column chromatography (developing solution is a mixed solution of dichloromethane/methanol in a volume ratio of 14:1->13:1->12:1) to obtain a final product of 634.2 mg, with yield 51%.

Embodiment 2, TG1 is Determined by the Nuclear Magnetic Resonance

Figure 2A:
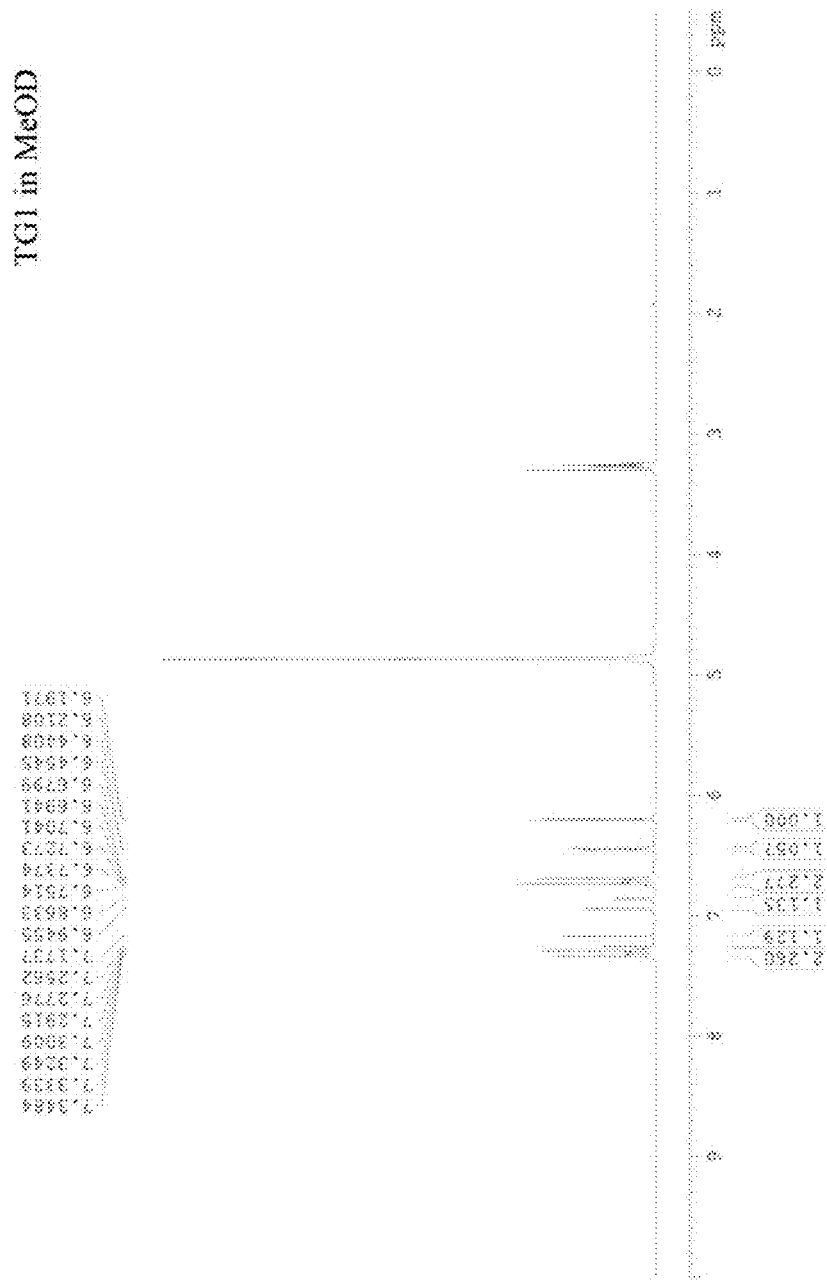
FIG. 2a and FIG. 2b show that the product TG1 (2, 3, 5, 4'-tetrahydroxy-trans-stilbene) is dissolved in MeOD (about 0.4 ml), placed in a nuclear magnetic resonance measuring tube, and determined at room temperature on DPX-200 NMR spectrometer.
Figure 2B:
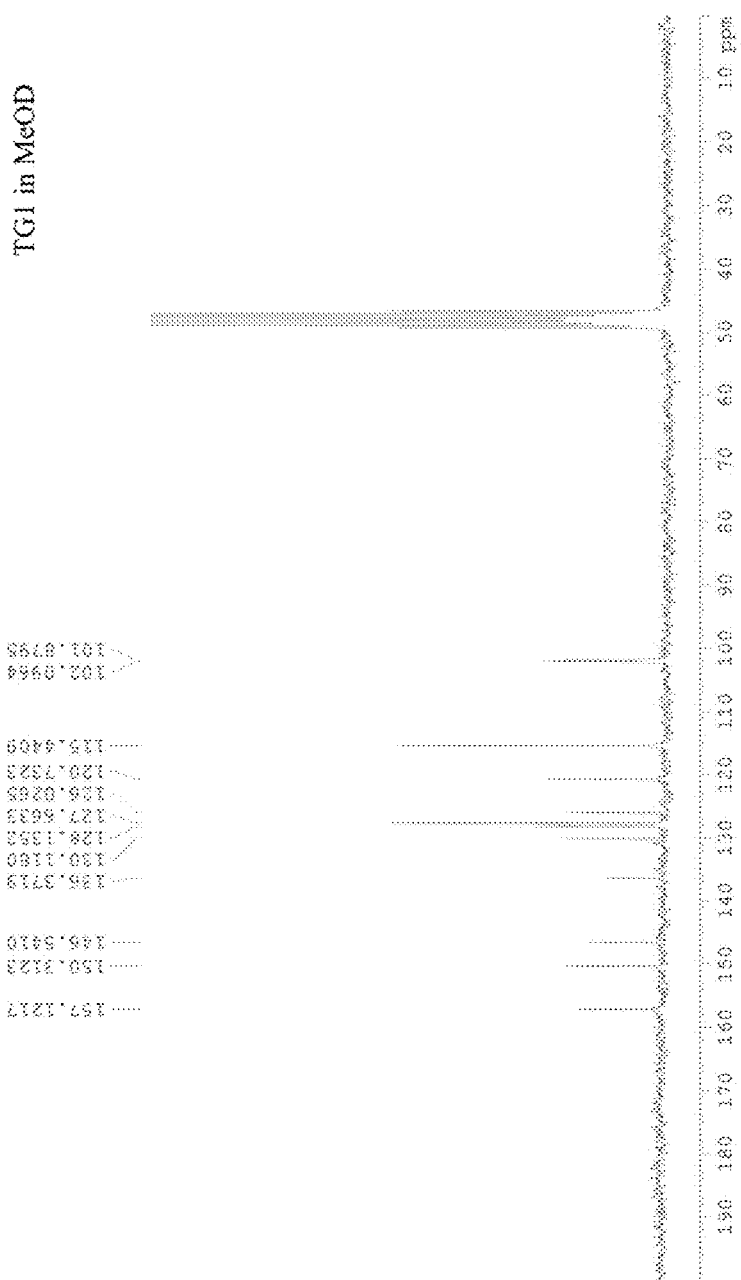
Figure 3:
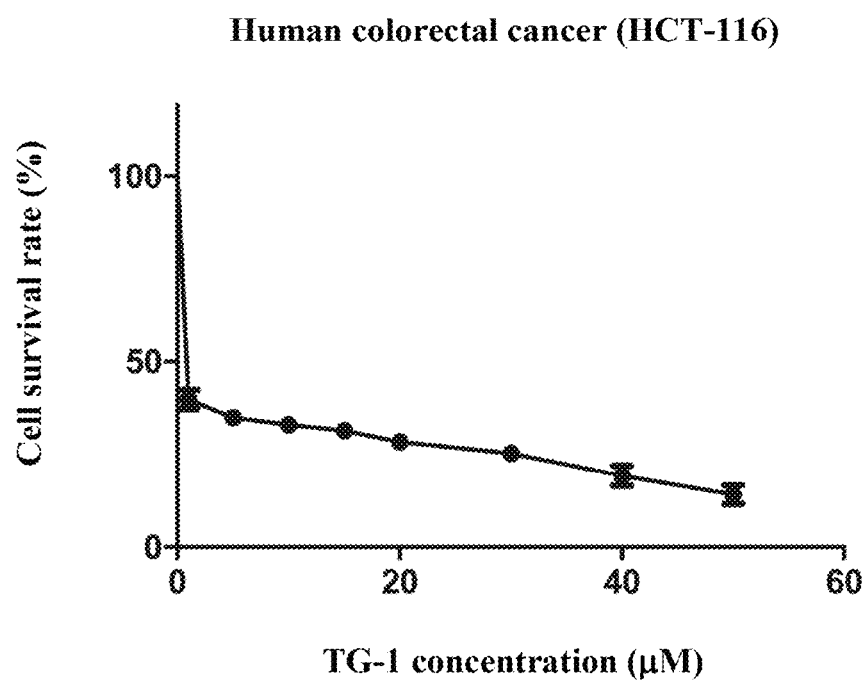
FIG. 3 shows that the pharmaceutical compound TG1 is administered to the human colorectal cancer cell line HCT-116, and its inhibitory ability is detected. The MTT assay results show that the $IC_{50}$ value is as low as 0.031 μM, which means that the pharmaceutical compound TG1 can inhibit 50% of the colorectal cancer cell line HCT-116 at 0.031 μM.
Figure 4:
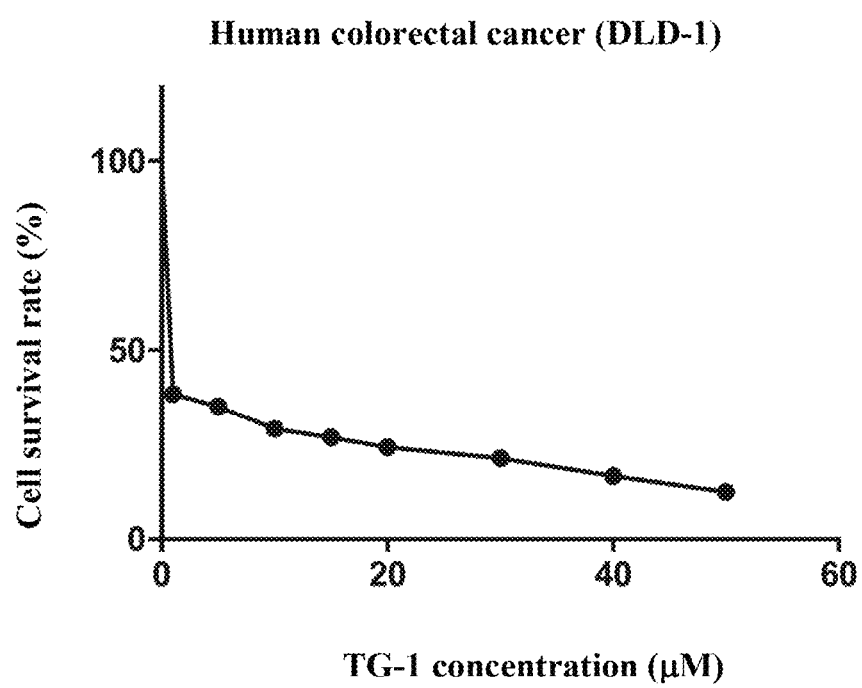
FIG. 4 shows that the pharmaceutical compound TG1 is administered to the human colorectal cancer cell line DLD-1, and the inhibitory ability thereof is detected. The MTT assay result shows that the $IC_{50}$ value is 0.056 μM, which means that the pharmaceutical compound TG1 can inhibit 50% of the colorectal cancer cell line DLD-1 at 0.056 μM.
Figure 5:
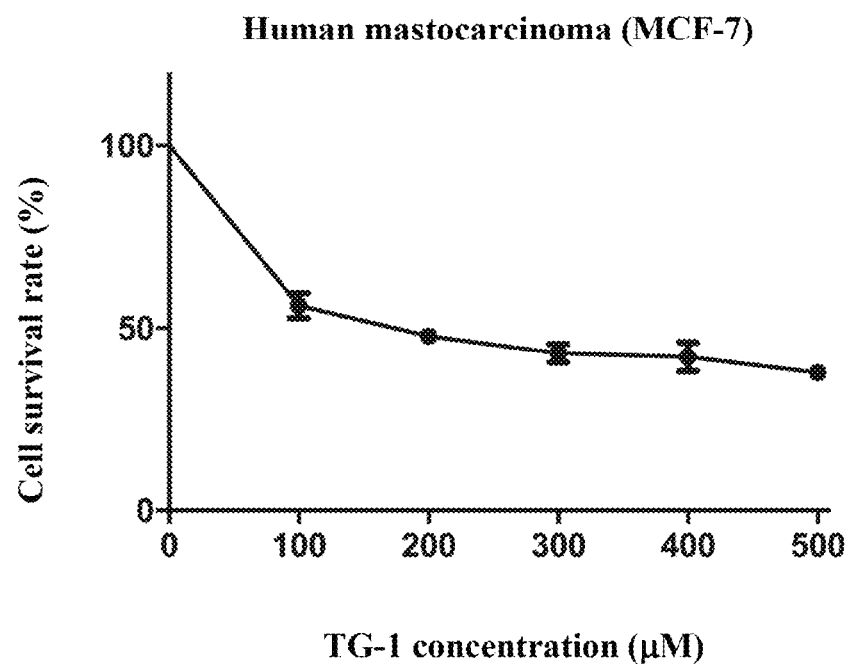
FIG. 5 shows that the pharmaceutical compound TG1 is administered to the human breast cancer cell line MCF-7, and the inhibitory ability thereof is detected. The MTT assay results show that the $IC_{50}$ value is 190 μM, which means that the pharmaceutical compound TG1 can inhibit 50% of human mastocarcinoma cell line MCF-7 at 190 μM, its concentration is quite high, no significant effect.
Figure 6:
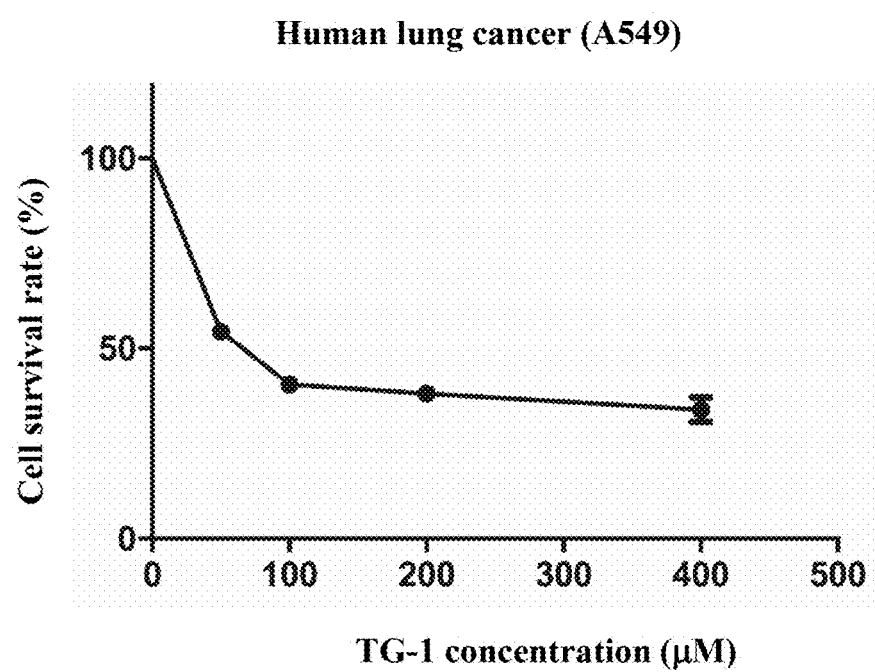
FIG. 6 shows that the pharmaceutical compound TG1 is administered to the human lung cancer cell line A549, and the inhibitory ability thereof is detected. The MTT assay results show that the $IC_{50}$ value is 63 μM, which means that the pharmaceutical compound TG1 can inhibit 50% of human lung cancer cell line A549 at 63 μM, no significant inhibition effect on lung cancer cells.
Figure 7:
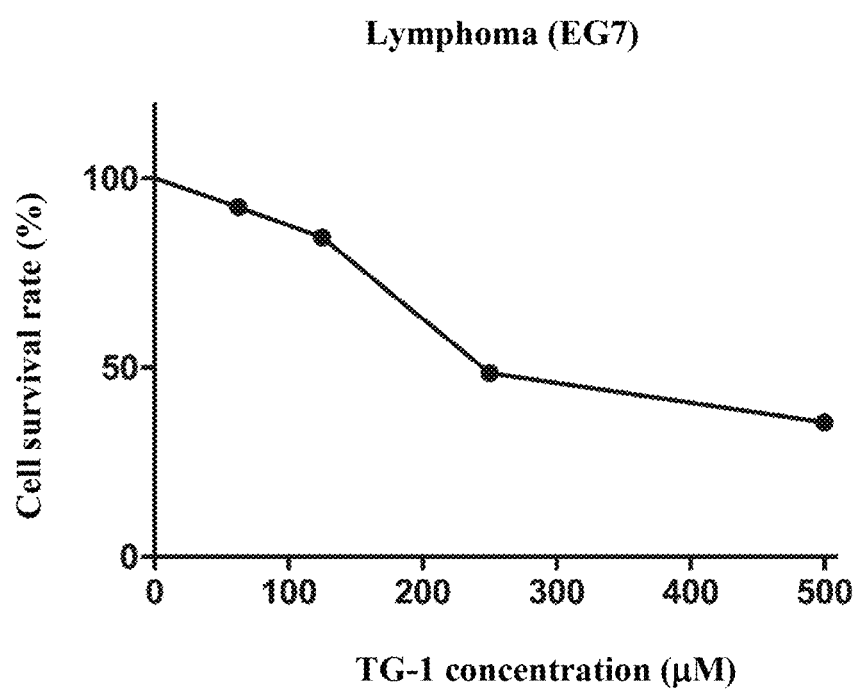
FIG. 7 shows that the pharmaceutical compound TG1 is administered to the lymphoma cell line E.G7, and the inhibitory ability thereof is detected. The MTT assay results show that the pharmaceutical compound TG1 has no specific inhibitory ability against lymphatic cancer cells, and the $IC_{50}$ value is 180 μM, which means that the pharmaceutical compound TG1 can inhibit 50% of lymphoid cancer cell line E.G7 at 180 μM, no significant inhibition effect on lymphatic cancer cell.
Figure 8:
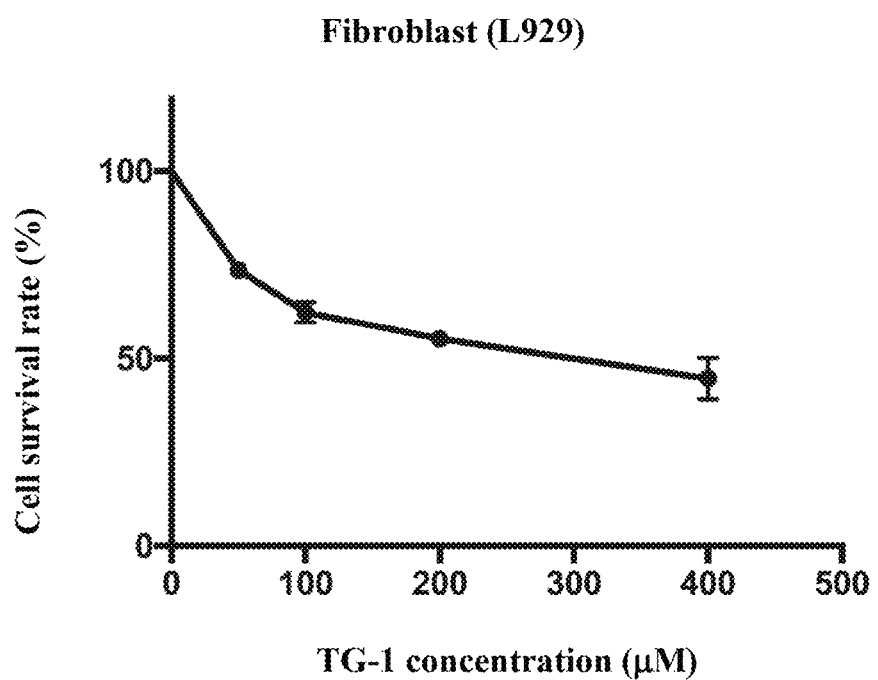
FIG. 8 shows that the pharmaceutical compound TG1 is administered to the fibroblast cell line L929, and the inhibitory ability thereof is detected. The MTT assay results show that the pharmaceutical compound TG1 has no specific inhibitory ability against fibroblast cell, and the $IC_{50}$ value is 255 μM, which means that the pharmaceutical compound TG1 can inhibit 50% of fibroblast cell line L929 at 255 μM, no significant inhibition effect on fibroblast cell.

Referring to FIG. 2a and FIG. 2b, the product is dissolved in MeOD (about 0.4 ml), placed in a nuclear magnetic resonance measuring tube, and determined on a DPX-200 nuclear magnetic resonance apparatus at room temperature. 1H NMR (200 MHz, MeOD) δ 7.31, 6.72 (dt, J=8.5, 2.9, 1.8 Hz; J=8.7, 2.8, 2.0 Hz 2H; 2H, H-2', H-6', H-3', H-5'), 7.21, 6.90 (d, J=16.5 Hz; J=16.4 Hz, 1H; 1H, H-7, H-8), 6.45, 6.20 ppm (d, J=2.7 Hz; J=2.7 Hz, 1H; 1H, H-3, H-5); 13C NMR (50 MHz, MeOD) δ 157.1, 150.3, 146.5, 136.4 (C2, C4, C6, C4'), 130.1, 126.0 (C1, C1'), 128.1, 120.7 (C7, C8), 127.7, 115.4 (C2', C3', C4', C5'), 102.1, 101.9 ppm (C3, C5).

Embodiment 3, Effect of TG1 on Colorectal Cancer Cells

The cell line HCT-116 is an adult colorectal cancer cell, and its cells are TGF-β1 and TGF-β2, which are the targeted cells commonly used in preclinical colorectal cancer; the cell line DLD-1 is a male human colorectal cancer. The cells, which are cancer cells that have invaded the lymph nodes in the late stage, have rapid metastatic growth and are also the targeted cells commonly used in preclinical studies of colorectal cancer; the cell line MCF-7 is an adult female mastocarcinoma cell with Tx-4 oncogene, which is a targeted cell commonly used in preclinical studies of mastocarcinoma. The cell line A549 is an adult male lung cancer cell, and its cell characteristic is the ability to synthesize lecithin. Pre-clinical studies of targeted cells are commonly used in lung cancer; cell line EG7 is a lymphoma cell, and its cells with antigen OVA are the targeted cells commonly used in cancer immunotherapy for preclinical studies; cell line L929 is fibroblast, which is the specified cell for preclinical studies of the cytotoxicity standard assay.

Assay Method:
Cell Viability by MTT Assay

1) On the previous day, the cancer cells are cultured on a 24- or 48-well plate for 24 hours, and the number of cells is $10^4$ cells/well, so that the cancer cells are completely attached to the well plate.

2) The culture solution is extracted, and the culture solution containing the pharmaceutical compound TG1 at different concentrations is added to allow the cells and the drug to act in the incubator for 24 hours.

3) The culture solution is extracted, and the culture solution containing 10% MTT is added, and it is taken out in an incubator and protected from light for 4 hours.

4) The culture solution is extracted, and DMSO is added to dissolve the purple crystals, and the light absorption value is measured at a wavelength of 570 nm.

5) The cell survival rate and $IC_{50}$ of the drug are calculated by comparing the values of the control group with the light absorption values of different groups.

6) The cell survival rate and $IC_{50}$ of the combined drug at this ratio are calculated by comparing the values of the control group with the light absorption values of different groups.

7) The drug combination index is calculated by The Combination Index Theorem formula.

Assay Results (See FIG. 3~FIG. 8):

Pharmaceutical compound TG1 is administered to human colorectal cancer cell line HCT-116, and the inhibitory ability thereof is detected. The MTT assay results show that the pharmaceutical compound TG1 can poison colorectal cancer cells at low drug concentration with $IC_{50}$ value as low as 0.031 μM, which means that the pharmaceutical compound TG1 can inhibit 50% of colorectal cancer cell line HCT-116 at 0.031 μM, it, with considerable poisoning ability (as shown in Table 1 and FIG. 3).

The pharmaceutical compound TG1 is administered to the human colorectal cancer cell line DLD-1, and the inhibitory ability thereof is detected. The cell survival rate assay (MTT assay) shows that the pharmaceutical compound TG1 has a significant ability to poison colorectal cancer cells at a low concentration, and the $IC_{50}$ value is 0.056 μM, the effect is quite outstanding (as shown in Table 1 and FIG. 4).

However, the pharmaceutical compound TG1 is administered to the human mastocarcinoma cell line MCF-7, and the inhibitory ability thereof is detected. The cell survival rate assay (MIT assay) results show that the pharmaceutical compound TG1 has no special inhibitory ability against human mastocarcinoma cells, and the $IC_{50}$ value is 190 μM, the drug concentration is quite high, no significant effect (as shown in Table 1 and FIG. 5).

However, the pharmaceutical compound TG1 is administered to the human lung cancer cell line A549, and the inhibitory ability thereof is detected. The cell survival rate assay (MTT assay) results show that the pharmaceutical compound TG1 has no specific inhibitory ability against human lung cancer cells, and the $IC_{50}$ value is 63 μM, which means no significant inhibition effect on lung cancer cell (as shown in Table 1 and FIG. 6).

However, the pharmaceutical compound TG1 is administered to the lymphoma cell line E.G7, and the inhibitory ability thereof is detected. The cell survival rate assay (MIT assay) results show that the pharmaceutical compound TG1 has no specific inhibitory ability against lymphatic cancer cells, and the $IC_{50}$ value is 180 μM, which means no significant inhibition effect on lymphatic cancer cells (as shown in Table 1 and FIG. 7).

However, the pharmaceutical compound TG1 is administered to the fibroblast cell line L929, and the inhibitory ability thereof is detected. The cell survival rate assay (MTT assay) results show that the pharmaceutical compound TG1 has no specific inhibitory ability against fibroblasts, and the $IC_{50}$ value is 255 μM, which means no significant inhibition effect on fibroblast (as shown in Table 1 and FIG. 8).

Further analysis of the drug concentration required to inhibit half of cancer cells is shown as $IC_{50}$ value (as shown in Table 1), TG1 drug has significant inhibitory effect on growth of different types of human colorectal cancer cell at a relatively low drug concentration, and in reverse no obvious effect on other cancers such as lung cancer cells, mastocarcinoma cells or fibroblasts.

TABLE 1

| $IC_{50}$ value of pharmaceutical compound TG1 for different cancer cells | |
|---|---|
| Cancer cell line | $IC_{50}$ |
| HCT116 Colorectal cells | 0.031 μM |
| DLD-1 Colorectal cells | 0.056 μM |
| MCF-7 Breast cancer cells | 190 μM |
| A549 Lung cancer cells | 63 μM |
| EG7 Lymphoma cells | 180 μM |
| L929 Fibroblast cells | 255 μM |

According to the above assay results, the pharmaceutical compound TG1 disclosed by the present invention has a highly specific poisoning ability against colorectal cancer cells, and its ability to poison colorectal cancer cells is 1000-6000 times higher than that of other cells.

TG1 inhibits the β-catenin message pathway to promote the cancer apoptosis, mainly to increase the proportion of Bax/Bcl-2 in cells, increase the activation of caspase-3, so as to split the DNA repairase PARP, thereby opening the cancer cell apoptosis effect.

Embodiment 4, Using Animal Assay to Evaluate the Inhibitory Effect of TG1 on Colorectal Cancer The mouse is used as a model organism to observe the inhibition growth of TG1 on colorectal cancer tumors. The human colorectal cancer cell (HT-29) is implanted in the back of mouse (nu/nu mouse), when the tumors are grown to about 250 mm³, TG1 (10 mg/kg) or clinical treatment drug Irinotecan (10 mg/kg) is administered to the tail vein of mouse twice a week, comparing the effect of the untreated group (Control) and treatment group (TG1 or Irinotecan) to inhibit the growth of colorectal cancer cells, and only 8 mice are observed in each group.

Animal Assay Method:

1) The human colorectal cancer cell (HT-29) is implanted in the back of mouse (nu/nu mouse), and the tumors are grown to about 250 mm$^3$ for grouping.

2) The mice are divided into 3 groups (untreated group, treatment group TG1 and clinical anticancer drug Irinotecan of treatment group), 8 mice in each group.

3) The treatment group TG1 and Irinotecan are administered at a concentration of 10 mg/kg, and the drug is administered in the tail vein at a frequency of 2 times per week.

4) Observe the tumor volume growth, the tumor volume calculation formula is: length×width×width×0.5.

Figure 9:
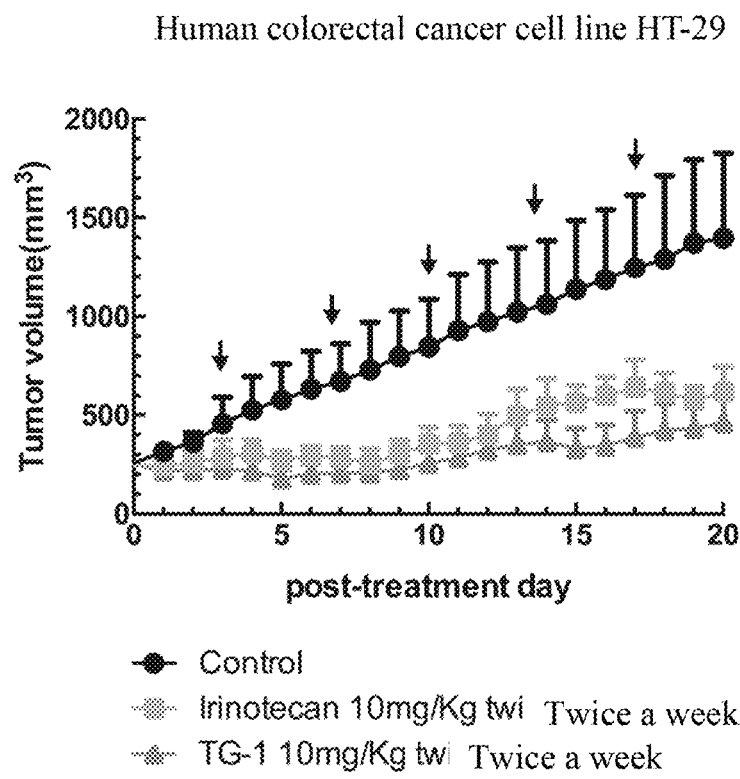
FIG. 9 shows that the mouse is used as model organism to observe the growth of colorectal cancer tumors in the untreated group (Control) and the treatment group (TG1 or Irinotecan).

Assay results (Referring to FIG. 9): it is known by measuring the tumor volume that the colorectal cancer of the untreated group is grown rapidly, and the average volume of the tumor volume is measured on the 10$^{th}$ day, which is about 846 mm$^3$. The treatment group can effectively inhibit tumor growth, wherein, the mean tumor volume is 291 mm$^3$ on the 10$^{th}$ day in the TG1 group and about 327 mm$^3$ on the 10$^{th}$ day in the Irinotecan group. On the 15$^{th}$ day, the mean volume of the untreated group is more than 1100 mm$^3$, and the treatment group is still very effective in inhibiting tumor growth, wherein, the average tumor volume measured on the 15$^{th}$ day in the TG1 group is 300 mm$^3$, and 600 mm$^3$ the 15$^{th}$ day in the Irinotecan group. On the 20$^{th}$ day, the mean volume of the untreated group is more than 1400 mm$^3$, and the treatment group is still very effective in inhibiting tumor growth, wherein, the average tumor volume measured on the 20$^{th}$ day in the TG1 group is 461 mm$^3$, and 617 mm$^3$ the 20$^{th}$ day in the Irinotecan group. The animal assay results show that the pharmaceutical compound TG1 disclosed in the present invention has a relatively good inhibitory effect against human colorectal cancer.

In summary, the product TG1 is obtained by modifying the functional group by THSG, and the cell survival rate assay (MTT assay) results show that the pharmaceutical compound TG1 has a highly specific ability to poison human colorectal cancer cells; on the contrary, for other species, such as mastocarcinoma, lung cancer and lymphoma, the pharmaceutical compound TG1 has no significant effect to inhibit the growth. Further, it is known from animal assay results that the pharmaceutical compound TG1 disclosed by the present invention provides an effect of inhibiting the growth of colorectal cancer tumors similar to or more excellent than the current cancer drug Irinotecan, as compared with the control group. It is disclosed by the present invention that it is expected to provide a highly specific pharmaceutical compound for poison colorectal cancer cells in the industry for the treatment of colorectal cancer.

All the features disclosed in the present invention should be realized in any combination mode. Each feature disclosed in the present invention should be replaced by the same, equivalent or similarly intended substitute. Therefore, unless otherwise explicitly stated, each disclosed feature is merely an embodiment of a class of equipollent or similar feature.

The invention claimed is:

1. A method for treating colorectal cancer in a subject, wherein the method comprising administrating to said subject a pharmaceutical composition, wherein the pharmaceutical composition comprising a compound as shown in Eq. I

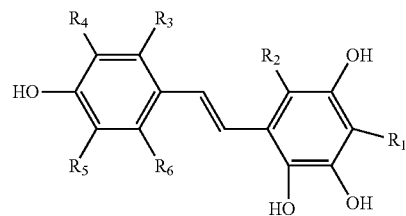

Eq. I wherein R1, R2, R3, R4, R5 and R6 are —H.

2. The method of claim 1, wherein the method is for treating rectal cancer.

3. The method of claim 1, wherein the method includes a mode of administration, the mode of administration comprises a dose and an administration interval, the dose is 10 mg/kg, the administration interval is twice a week, according to a cyclic administration.

4. The method of claim 1, wherein the method has a specific effect of inhibiting growth of colorectal cancer cells and tumors, and its efficacy is to reduce a tumor volume of colorectal cancer by 50-73%.

5. The method of claim 2, wherein the method has the specific effect of inhibiting growth of rectal cancer cells and tumors, and its efficacy is to reduce a tumor volume of rectal cancer by 50-73%.

* * * * *